United States Patent
Kilian et al.

(10) Patent No.: US 9,999,221 B2
(45) Date of Patent: *Jun. 19, 2018

(54) HERBICIDE COMBINATION CONTAINING PELARGONIC ACID AND DEFINED ALS INHIBITORS

(71) Applicant: BAYER CROPSCIENCE AKTIENGESELLSCHAFT, Monheim am Rhein (DE)

(72) Inventors: Michael Kilian, Leverkusen (DE); Christian Marienhagen, Langenfeld (DE)

(73) Assignee: BAYER CROPSCIENCE AKTIENGESELLSCHAFT, Monheim am Rhein (DE)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/382,015

(22) Filed: Dec. 16, 2016

(65) Prior Publication Data

US 2017/0094966 A1 Apr. 6, 2017

Related U.S. Application Data

(63) Continuation of application No. 14/897,971, filed as application No. PCT/EP2014/064503 on Jul. 8, 2014, now Pat. No. 9,609,865.

(30) Foreign Application Priority Data

Jul. 12, 2013 (EP) .................................... 13176240

(51) Int. Cl.
*A01N 37/02* (2006.01)
*A01N 47/36* (2006.01)
*A01N 47/38* (2006.01)
*A01N 47/30* (2006.01)

(52) U.S. Cl.
CPC .............. *A01N 37/02* (2013.01); *A01N 47/30* (2013.01); *A01N 47/36* (2013.01); *A01N 47/38* (2013.01)

(58) Field of Classification Search
CPC ........ A01N 37/02; A01N 47/38; A01N 47/36; A01N 47/30
See application file for complete search history.

(56) References Cited

U.S. PATENT DOCUMENTS 5,106,410 A 4/1992 Puritch et al.
6,503,869 B1 1/2003 Beste et al.

FOREIGN PATENT DOCUMENTS

CN 102217626 A 10/2011
EP 0494386 A1 7/1992
WO 2008142391 A1 11/2008

OTHER PUBLICATIONS

International Search Report from corresponding PCT/EP2014/064503, dated Sep. 16, 2014.
International Search Report from PCT/EP2014/064504, dated Sep. 24, 2014.
Database WPI Week 201241, Thomson Scientific, London, GB, AN 2011-P33732, XP002712978.
European Search Report from corresponding EP 13 17 6240, dated Sep. 16, 2011.
Equip Corn Herbicide Product Sheet, Dec. 2004, Bayer CropScience, pp. 1-11.

*Primary Examiner* — John Pak
*Assistant Examiner* — Andriae M Holt
(74) *Attorney, Agent, or Firm* — McBee Moore Woodward & Vanik IP, LLC

(57) ABSTRACT

The present invention relates to a herbicide combination comprising at least pelargonic acid and at least one ALS inhibitor selected from the group consisting of iodosulfuron-methyl, foramsulfuron, mesosulfuron-methyl, flazasulfuron, amidosulfuron, ethoxysulfuron and thiencarbazone-methyl.

11 Claims, No Drawings

HERBICIDE COMBINATION CONTAINING PELARGONIC ACID AND DEFINED ALS INHIBITORS

CROSS REFERENCE TO RELATED APPLICATIONS

This application is a continuation application of U.S. application Ser. No. 14/897,971, filed Dec. 11, 2015, which is a § 371 National Stage Application of PCT/EP2014/064503, filed 8 Jul. 2014, which claims priority to EP 13176240.3, filed 12 Jul. 2013, the contents of which are incorporated herein in their entireties.

BACKGROUND

Field of the Invention

The present invention is in the technical field of crop protection compositions which can be employed against unwanted vegetation, for example by the post-emergence method in sown and/or planted crop plants, in fruit plantations (plantation crops), on non-crop areas (e.g. squares of residential areas or industrial sites, rail tracks) and on lawns. In addition to the single application, sequential applications are also possible.

Description of Related Art

The present invention relates to a herbicide combination comprising at least two herbicides and its application for controlling unwanted vegetation, in particular a herbicide combination comprising at least pelargonic acid and at least one ALS inhibitor selected from the group consisting of iodosulfuron-methyl, foramsulfuron, mesosulfuron-methyl, flazasulfuron, amidosulfuron, ethoxysulfuron and thiencarbazone-methyl.

Herbicidally active fatty acids are known from the prior art (e.g. WO01/05472).

A compound from the substance class of the ALS inhibitors inhibits the enyzme acetolactate synthase (ALS) which is responsible for the biosynthesis of branched amino acids such as L-valine, L-leucine and L-isoleucine. Therefore, this substance class—in addition to other substance classes—is, according to its mechanism of action, assigned to the group of the ALS (acetolactate synthase) inhibitors (see also http://www.hracglobal.com/Portals/5/moaposter.pdf). The ALS inhibitors include, for example, the sulfonylureas (see also, for example, "The Pesticide Manual" 15th, Edition, British Crop Protection Council 2011). These herbicides are in particular frequently applied on fields cultivated with soybeans and cereals. Uptake of these herbicides is via the roots and leaves.

The herbicidal activity of such herbicides against harmful plants (broad-leaved weeds, weed grasses, cyperaceae; hereinbelow together also referred to as "weed") is already on a high level, but generally depends on the application rate, the respective preparation form, the respective harmful plants to be controlled or the spectrum of harmful plants, the climatic and soil conditions, etc. Further criteria in this context are duration of action, or the breakdown rate, of the herbicide, the general crop plant compatibility and speed of action (more rapid onset of action), the activity spectrum and behavior toward follower crops (replanting problems) or the general flexibility of application (control of weeds in their various growth stages). If appropriate, changes in the susceptibility of harmful plants, which may occur on prolonged use of the herbicides or in limited geographical regions (control of tolerant or resistant weed species), may also have to be taken into account. The compensation of losses in action in the case of individual plants by increasing the application rates of the herbicides is only possible to a certain degree, for example because such a procedure reduces the selectivity of the herbicides or because the action is not improved, even when applying higher rates.

Thus, there is frequently a need for targeted synergistic activity against specific weed species, weed control with better overall selectivity, generally lower amounts of active compounds used for equally good control results and for a reduced active compound input into the environment to avoid, for example, leaching and carry-over effects. There is also a need for developing one-shot applications to avoid labor-intensive multiple applications, and also to develop systems for controlling the rate of action, where, in addition to an initial rapid control of weeds, there is also a slow, residual control.

A possible solution to the problems mentioned above may be to provide herbicide combinations, that is mixtures of a plurality of herbicides and/or other components from the group of the agrochemically active compounds of a different type and of formulation auxiliaries and additives customary in crop protection which contribute the desired additional properties. However, in the combined use of a plurality of active compounds, there are frequently phenomena of chemical, physical or biological incompatibility, for example lack of stability in a joint formulation, decomposition of an active compound or antagonism in the biological activity of the active compounds. For these reasons, potentially suitable combinations have to be selected in a targeted manner and tested experimentally for their suitability, it not being possible to safely discount a priori negative or positive results.

SUMMARY

It was the object of the present invention to provide crop protection compositions as alternatives to the prior art, or as an improvement thereof.

Surprisingly it has now been found that this object can be achieved by the combination of pelargonic acid and at least one ALS inhibitor, selected from the group consisting of iodosulfuron-methyl, foramsulfuron, mesosulfuron-methyl, flazasulfuron, amidosulfuron, ethoxysulfuron and thiencarbazone-methyl, which interact in a particularly favorable manner; for example when they are employed for controlling unwanted vegetation in sown and/or planted crop plants, greens/lawns, in fruit plantations (plantation crops) or on non-crop areas (e.g. squares of residential areas or industrial sites, rail tracks. Surprisingly, the activity of the combinations according to the invention of two active compounds, when used against weeds, is higher than the activities of the individual components. A true synergistic effect which could not have been predicted therefore exists, not just a complementation of action (additive effect).

Pelargonic acid (nonanoic acid) is a saturated fatty acid or carboxylic acid derived from the alkane n-nonane. It is an alkanoic acid which is liquid under standard conditions and is herbicidally active. Preference is given according to the invention to using pelargonic acid in unhydrolyzed form.

ALS inhibitors which are used according to the invention are selected from the group consisting of iodosulfuron-methyl (IUPAC name: 4-iodo-2-[(4-methoxy-6-methyl-1,3,5-triazin-2-yl)carbamoylsulfamoyl]benzoate, sodium salt), foramsulfuron (IUPAC name: 1-(4,6-dimethoxypyrimidin-2yl)-3-(2-dimethylcarbamoyl-5-formamidophenylsulfonyl) urea, mesosulfuron-methyl (IUPAC name: methyl 2-[(4,6-dimethoxypyrimidin-2-ylcarbamoyl)sulfamoyl]-a-

(methanesulfonamido)-p-toluate), flazasulfuron (IUPAC name: 1-(4,6-dimethoxypyrimidin-2-yl)-3-(3-trifluoromethyl-2-pyridylsulfonyl)urea), amidosulfuron (IUPAC: 3-(4,6-dimethoxypyrimidin-2-yl)-1-(N-methyl-N-methylsulfonylaminosulfonyl)urea), ethoxysulfuron (IUPAC name: 2-ethoxyphenyl[(4,6-dimethoxypyrimidin-2-yl)carbamoyl]sulfamate) and thiencarbazone methyl (IUPAC name: methyl 4-[(4,5-dihydro-3-methoxy-4-methyl-5-oxo-1H-1,2,4-triazol-1 yl)carbonylsulfamoyl]-5-methylthiophene-3-carboxylate).

Particular preference is given to using iodosulfuron-methyl (especially the sodium salt) and/or foramsulfuron and especially to using iodosulfuron-methyl (especially the sodium salt) and foramsulfuron together. The invention also encompasses combinations of ALS inhibitors and especially of two or more sulfonylureas having complementary activity spectra.

Hereinbelow, the terms "herbicide(s)", "individual herbicide(s)", "compound(s)" or "active compound(s)" are also used synonymously for the term "components(s)" in the context.

Additionally, the herbicide combination according to the invention may comprise further components, for example agrochemically active compounds of a different type and/or the formulation auxiliaries and/or additives customary in crop protection, or may be used together with these. Hereinbelow, the use of the term "herbicide combination(s)" or "combination(s)" also includes the "herbicidal compositions" formed in this manner.

DETAILED DESCRIPTION OF A PREFERRED EMBODIMENT

In a preferred embodiment, the herbicide combination according to the invention comprises an effective amount of at least pelargonic acid and at least one of the above-mentioned ALS inhibitors and/or has synergistic activities. The synergistic actions can be observed, for example, in the case of joint application, for example as a ready-to-use formulation, co-formulation or as a tank mix; however, they can also be observed when the active compounds are applied at different times (splitting) (packed, for example, as combipack or monodoses). It is also possible to apply the herbicides or the herbicide combination in a plurality of portions (sequential application), for example post-emergence applications or early post-emergence applications followed by medium or late post-emergence applications. Here, the joint application of the herbicide combination according to the invention is preferred. Substances attracting protons (fatty acids, among others) destabilize sulfonylureas. This means that sulfonylureas and fatty acids cannot, or only with great difficulties, be formulated together as a solo formulation, which requires certain demands with regard to the packaging of the crop protection composition to be met. If fatty acids and sulfonylurea are, as in the tests, to be applied as tank mixes, it has to be ensured that the spray liquor is applied relatively quickly after preparation.

The synergistic effects permit a reduction of the application rates of the individual herbicides, a higher and/or longer efficacy at the same application rate, the control of species which were as yet uncontrolled (gaps), control of species which are tolerant or resistant to individual herbicides or to a number of herbicides, an extension of the period of application and/or a reduction in the number of individual applications required and—as a result for the user—weed control systems which are more advantageous economically and ecologically.

In the herbicide combination according to the invention, the application rate of the pelargonic acid may vary within a wide range; for example, the application rate should be at least 2500 g of AS/ha (hereinbelow, AS/ha means "active substance per hectare"=based on 100% active compound), but preferably between 2500 and 30000 g of AS/ha, more preferably between 10000 and 30000 g of AS/ha and most preferably between 20000-30000 g of AS/ha.

In the herbicide combination according to the invention, the application rate of the above-mentioned herbicidally active ALS inhibitor may vary within a wide range, for example between 1 g and 200 g of AS/ha, with a relatively wide spectrum of harmful plants being controlled.

If foramsulfuron is used, the application rate is preferably in a range of 15-60 g of AS/ha and even more preferably between 30-60 and particularly preferably between 30-45 g of AS/ha.

If iodosulfuron is used, the application rate is preferably in a range of 1 and 10 g of AS/ha and even more preferably between 1-5 g of AS/ha.

If mesosulfuron is used, the application rate is preferably in a range of 7.5 and 30 g of AS/ha.

If thiencarbazone is used, the application rate is preferably in a range of 10 and 30 g of AS/ha.

If flazasulfuron is used, the application rate is preferably in a range of 10 and 50 g of AS/ha.

If amidosulfuron is used, the application rate is preferably in a range of 30 and 60 g of AS/ha.

If ethoxysulfuron is used, the application rate is preferably in a range of 60 and 200 g of AS/ha.

Ranges of suitable ratios of the pelargonic acid and the herbicidally active ALS inhibitor can be found, for example, by looking at the application rates mentioned for the individual compounds. In the combination according to the invention, the application rates can generally be reduced. Preferred mixing ratios of the pelargonic acid (hereinbelow referred to as component "A" or just as "A") and above-mentioned herbicidally active ALS inhibitor (hereinbelow referred to as component "B" or just as "B") described according to the invention in the combination according to the invention are characterized by the following weight ratios:

The weight ratio (A):(B) of the components (A) and (B) is generally in the range of from 30000:1 to 12.5:1, preferably 30000:1 to 50:1.

The following weight ratios apply to the preferred combinations of pelargonic acid plus ALS inhibitor.

When using pelargonic acid and foramsulfuron, the weight ratio is preferably in the range from 2000:1 to 167:1 and even more preferably in the range from 1000:1 to 333:1 and particularly preferably in the range from 1000:1 to 444:1.

When using pelargonic acid and iodosulfuron, the weight ratio is preferably in a range from 30000:1 to 1000:1 and even more preferably in the range from 30000:1 to 4000:1.

When using pelargonic acid and mesosulfuron, the weight ratio is preferably in a range from 4000:1 to 333:1.

When using pelargonic acid and thiencarbazone, the weight ratio is preferably in a range from 3000:1 to 333:1.

When using pelargonic acid and flazasulfuron, the weight ratio is preferably in a range from 3000:1 to 200:1.

When using pelargonic acid and amidosulfuron, the weight ratio is preferably in a range from 1000:1 to 167:1.

When using pelargonic acid and ethoxysulfuron, the weight ratio is preferably in a range from 500:1 to 50:1.

Preference is given to herbicide combinations which, in addition to the combination according to the invention, also comprise one or more further agrochemically active compounds which also act as a selective herbicide. Particular preference is given to using the combination of pelargonic acid and of at least two of the above-mentioned ALS inhibitors, preferably both foramsulfuron and iodosulfuron.

In the particularly preferred combination of pelargonic acid with foramsulfuron and iodosulfuron-methyl (especially the sodium salt), 15-60 parts by weight of the active compound foramsulfuron and 2500-30000 (preferably 10000-30000, particularly preferably 10000-15000) parts by weight of the pelargonic acid are present per 1 (one) part by weight of iodosulfuron-methyl. Surprisingly, it has also been found in particular that even small amounts of the pelargonic acid (10000 g-15000 g of AS/ha) together with foramsulfuron and iodosulfuron-methyl have synergistic effects.

The herbicide combination according to the invention may furthermore comprise, as additional further components, various agrochemically active compounds, for example from the group of the safeners, fungicides, insecticides, acaricides, nematicides, bird repellants, soil structure improvers, plant nutrients (fertilizers), and herbicides and plant growth regulators which differ structurally from the herbicidally active compounds employed in accordance with the invention, or from the group of the formulation auxiliaries and additives customary in crop protection.

The active compound combinations according to the invention have very good herbicidal properties and can be used for controlling weeds. Here, weeds are understood to mean all plants which grow at sites where they are unwanted.

The active compound combinations according to the invention can be used, for example, in connection with the following plants:

Dicotyledonous weeds of the genera: *Cassia, Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus, Sphenoclea, Taraxacum, Plantago, Epilobium, Rubus, Achillea, Rumex, Lotus, Bellis.*

Monocotyledonous weeds of the genera: *Echinochloa, Eriochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Dactyloctenium, Agrostis, Alopecurus, Apera, Aegilops, Phalaris.*

Mosses and algae

If the active compounds are applied post-emergence to the green parts of the plants, growth likewise stops drastically a very short time after the treatment, and the weed plants remain at the growth stage of the point of time of application, or they die completely after a certain time, so that in this manner weed infestation is eliminated very early and in a sustained manner.

Preferably, the active compound combinations according to the invention can be used as total herbicides for controlling weeds, for example in particular on non-crop areas such as paths, squares and also under trees and shrubs, rail tracks etc. The active compound combinations according to the invention are distinguished by an action which has a particularly quick onset and lasts for a long time.

The herbicide combination according to the invention can be prepared by known processes, for example as mixed formulations of the individual components, if appropriate with further active compounds, additives and/or customary formulation auxiliaries, which combinations are then applied in a customary manner diluted with water, or as tank mixes by joint dilution of the components, formulated separately or formulated partially separately, with water. Also possible is the split application of the separately formulated or partially separately formulated individual components. It is also possible to use the herbicides or the herbicide combination in a plurality of portions (sequential application), for example by the post-emergence method or early post-emergence applications followed by medium or late post-emergence applications. Preference is given to the joint use of the active compounds in the respective combination.

Substances attracting protons (fatty acids, among others) destabilize sulfonylureas. This means that sulfonylureas and fatty acids can not, or only with great difficulties, be formulated together as a solo formulation, which requires certain demands with regard to the packaging of the crop protection composition to be met. If fatty acid and sulfonylurea are, as in the tests, to be applied as tank mixes, it has to be ensured that the spray liquor is applied relatively quickly after preparation. A preferred variant of the invention relates to processes for controlling weeds where component (A) and component (B) of the herbicide combination according to the invention are mixed only shortly before application onto the weeds and/or their habitat. According to the invention, "shortly before application" means that component (A) and component (B) are mixed preferably less than 6 hours, more preferably less than 3 hours and even more preferably less than 1 hour before application onto the weeds and/or their habitat.

Other than that, the pelargonic acid and the at least one ALS inhibitor employed in accordance with the invention can be converted jointly or separately into customary formulations, such as solutions, emulsions, suspensions, powders, foams, pastes, granules, aerosols, natural and synthetic materials impregnated with active compound and microencapsulations in polymeric materials. The formulations may comprise the customary auxiliaries and additives.

These formulations are produced in a known manner, for example by mixing the active compounds with extenders, i.e. liquid solvents, pressurized liquefied gases and/or solid carriers, optionally with use of surfactants, i.e. emulsifiers and/or dispersants and/or foam formers.

If the extender used is water, it is also possible to use, for example, organic solvents as auxiliary solvents. Suitable liquid solvents are essentially: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example mineral oil fractions, mineral and vegetable oils, alcohols such as butanol or glycol and the ethers and esters thereof, ketones such as acetone, methyl ethyl ketone, methyl isobutyl ketone or cyclohexanone, strongly polar solvents such as dimethylformamide or dimethyl sulfoxide, and water.

Useful solid carriers include: for example ammonium salts and ground natural minerals, such as kaolins, clays, talc, chalk, quartz, attapulgite, montmorillonite or diatomaceous earth, and ground synthetic minerals, such as finely divided silica, alumina and silicates; useful solid carriers for granules include: for example crushed and fractionated natural rocks, such as calcite, marble, pumice, sepiolite, dolomite and synthetic granules of inorganic and organic flours, and granules of organic material, such as sawdust, coconut shells, corn cobs and tobacco stalks; useful emulsifiers and/or foam formers include: for example nonionic and anionic emulsifiers, such as polyoxyethylene fatty acid esters, polyoxyethylene fatty alcohol ethers, e.g. alkylaryl polyglycol ethers, alkylsulfonates, alkylsulfates, arylsulfonates and protein hydrolyzates; useful dispersants include: for example lignosulfite waste liquors and methylcellulose.

In the formulations, it is possible to use tackifiers such as carboxymethylcellulose, natural and synthetic polymers in the form of powders, granules or latices, such as gum arabic, polyvinyl alcohol and polyvinyl acetate, or else natural phospholipids such as cephalins and lecithins and synthetic phospholipids. Further additives may be mineral and vegetable oils.

It is possible to use colorants such as inorganic pigments, for example iron oxide, titanium oxide and Prussian blue, and organic colorants such as alizarin colorants, azo colorants and metal phthalocyanine colorants, and trace nutrients such as salts of iron, manganese, boron, copper, cobalt, molybdenum and zinc.

In general, the formulations comprise between 0.1 and 95% by weight of active compound, preferably between 0.2 and 90% by weight.

The herbicide combination according to the invention can be used as such, in the form of its formulations or in the use forms prepared therefrom by further dilution, such as ready-to-use solutions, suspensions, emulsions, powders, pastes and granules. Application is accomplished in a customary manner, for example by watering, spraying, atomizing or broadcasting.

The active compound combinations according to the invention are generally applied in the form of finished formulations. However, the active compounds contained in the active compound combinations can, as individual formulations, also be mixed during use, i.e. be applied in the form of tank mixes.

The good herbicidal action of the novel active compound combinations can be seen from the examples which follow. While the individual active compounds show weaknesses in their herbicidal action, all combinations show a very good action on weeds which exceeds a simple sum of actions.

A synergistic effect in herbicides is always present when the herbicidal action of the active compound combination exceeds the action of the active compounds when applied individually.

The expected activity of a given combination of two or three herbicides can be calculated as follows (cf. COLBY, S. R.: "Calculating synergistic and antagonistic responses of herbicide combinations", Weeds 15, pages 20-22, 1967):

If X=% damage by herbicide (A) at an application rate of m g/ha,
Y =% damage by herbicide (B) at an application rate of n g/ha,
Z =% damage by herbicide (C) at an application rate of r kg/ha,
E1=the expected damage by herbicides (A) and (B) at application rates of m and n kg/ha and,
E2=the expected damage by herbicides (A) and (B) and (C) at application rates of m and n and r kg/ha,
then for a combination:

$$E1 = X + Y - \frac{X \times Y}{100}$$

and for a combination of 3 active compounds:

$$E2 = X + Y + Z - \frac{(X \times Y * X \times Z * Y \times Z)}{100} + \frac{X \times Y \times Z}{10000}$$

If the actual damage exceeds the calculated value, the activity of the combination is superadditive, i.e. it shows a synergistic effect. In this case, the damage actually observed must exceed the values calculated using the above formulae for the expected damages E1 and E2.

The invention is illustrated by the examples below.

Use examples:

The following formulations of the active compounds involved are used:

pelargonic acid 186.7 EC (emulsifiable concentrate)
  Commercial formulation Bayer Garten 3 Stunden Bio-Unkrautfrei, approved inter alia in Germany—product licence holder W. Neudorff GmbH KG foramsulfuron 50 WG (water dispersible granule) standard granule formulation without adjuvants iodosulfuron 10 WG (water dispersible granule)
  (commercial formulation Destiny, approved inter alia in Australia—Bayer CropScience)

mesosulfuron 75 WG (water dispersible granule) standard granule formulation without adjuvants thiencarbazone 70 WG (water dispersible granule) standard granule formulation without adjuvants flazasulfuron 25 WG (water dispersible granule)
  (commercial formulation Chikara, approved inter alia in Germany—product licence holder ISK Biosciences)

amidosulfuron 75 WG (water dispersible granule)
  (commercial formulation Hoestar, approved inter alia in Germany—Bayer CropScience)

ethoxysulfuron 60 WG (water dispersible granule)
  (commercial formulation SunRice, approved inter alia in Italy—Bayer CropScience)

The active compound concentrations required for the tests are prepared by dilution with water. The tested active compound combinations are mixed shortly before their biological examination.

Post-emergence Test

Test plants of a height of 5 to 15 cm are sprayed with the preparation of active compound such that the particular amounts of active compound desired are applied per unit area. The concentration of the spray liquor is chosen such that the particular amounts of active compound desired are applied in 10001 of water/ha. After 48 days, the degree of damage to the plants is rated in % damage in comparison to the development of the untreated control. In the case of all herbicide combinations according to the invention, for most of the test plants synergistic actions are observed (see Tables 1 to 18).

TABLE 1

| Weed | Pelargonic acid 10000 g of active compound/ha; herbicidal effect [%] | Foramsulfuron 60 g of active compound/ha; herbicidal effect [%] | Herbicidal effect [%] calculated according to Colby | Herbicidal effect [%] found |
|---|---|---|---|---|
| Chenopodium | 0 | 13.3 | 13 | 81.7 |
| Festuca ovina | 0 | 58.3 | 58 | 91.7 |
| Plantago major | 0 | 33.3 | 33 | 53.3 |
| Taraxacum officinale | 6.7 | 75 | 77 | 91.7 |
| Poa annua | 0 | 73.3 | 73 | 81.7 |
| Trifolium repens | 0 | 60 | 60 | 60 |

Table 1: Herbicide combination according to the invention consisting of pelargonic acid and foramsulfuron.

TABLE 2

| Weed | Pelargonic acid 10000 g of active compound/ha; herbicidal effect [%] | Foramsulfuron 15 g of active compound/ha; herbicidal effect [%] | Herbicidal effect [%] calculated according to Colby | Herbicidal effect [%] found |
|---|---|---|---|---|
| Chenopodium | 0 | 0 | 0 | 65 |
| Festuca ovina | 0 | 6.7 | 7 | 70 |
| Plantago major | 0 | 0 | 0 | 26.7 |
| Taraxacum officinale | 6.7 | 45 | 49 | 78.3 |
| Poa annua | 0 | 18.3 | 18 | 45 |
| Trifolium repens | 0 | 18.3 | 18 | 35 |

Table 2: Herbicide combination according to the invention consisting of pelargonic acid and foramsulfuron

TABLE 3

| Weed | Pelargonic acid 30000 g of active compound/ha; herbicidal effect [%] | Foramsulfuron 60 g of active compound/ha; herbicidal effect [%] | Herbicidal effect [%] calculated according to Colby | Herbicidal effect [%] found |
|---|---|---|---|---|
| Chenopodium | 20 | 13.3 | 31 | 83.3 |
| Festuca ovina | 6.7 | 58.3 | 61 | 98 |
| Plantago major | 13.3 | 33.3 | 42 | 60 |
| Taraxacum officinale | 20 | 75 | 80 | 98 |
| Poa annua | 0 | 73.3 | 73 | 90 |
| Trifolium repens | 3.3 | 60 | 61 | 65 |

Table 3: Herbicide combination according to the invention consisting of pelargonic acid and foramsulfuron.

TABLE 4

| Weed | Pelargonic acid 30000 g of active compound/ha; herbicidal effect [%] | Foramsulfuron 15 g of active compound/ha; herbicidal effect [%] | Herbicidal effect [%] calculated according to Colby | Herbicidal effect [%] found |
|---|---|---|---|---|
| Chenopodium | 20 | 0 | 20 | 68.3 |
| Festuca ovina | 6.7 | 6.7 | 13 | 81.7 |
| Plantago major | 13.3 | 0 | 13 | 35 |
| Taraxacum officinale | 20 | 45 | 56 | 89.3 |
| Poa annua | 0 | 18.3 | 18 | 31.7 |
| Trifolium repens | 3.3 | 18.3 | 21 | 33.3 |

Table 4: Herbicide combination according to the invention consisting of pelargonic acid and foramsulfuron

TABLE 5

| Weed | Pelargonic acid 10000 g of active compound/ha; herbicidal effect [%] | Iodosulfuron-methyl 10 g of active compound/ha; herbicidal effect [%] | Herbicidal effect [%] calculated according to Colby | Herbicidal effect [%] found |
|---|---|---|---|---|
| Chenopodium | 0 | 40 | 40 | 91 |
| Festuca ovina | 0 | 6.7 | 7 | 23.3 |
| Plantago major | 0 | 53.3 | 53 | 83.3 |
| Taraxacum officinale | 6.7 | 85 | 86 | 97 |
| Poa annua | 0 | 0 | 0 | 10 |
| Trifolium repens | 0 | 80 | 80 | 90 |

Table 5: Herbicide combination according to the invention consisting of pelargonic acid and iodosulfuron-methyl

TABLE 6

| Weed | Pelargonic acid 10000 g of active compound/ha; herbicidal effect [%] | Iodosulfuron-methyl 1 g of active compound/ha; herbicidal effect [%] | Herbicidal effect [%] calculated according to Colby | Herbicidal effect [%] found |
|---|---|---|---|---|
| Chenopodium | 0 | 0 | 0 | 43.3 |
| Festuca ovina | 0 | 0 | 0 | 13.3 |
| Plantago major | 0 | 0 | 0 | 26.7 |
| Taraxacum officinale | 6.7 | 18.3 | 24 | 66.7 |
| Poa annua | 0 | 0 | 0 | 0 |
| Trifolium repens | 0 | 18.3 | 18 | 0 |

Table 6: Herbicide combination according to the invention consisting of pelargonic acid and iodosulfuron-methyl

TABLE 7

| Weed | Pelargonic acid 30000 g of active compound/ha; herbicidal effect [%] | Iodosulfuron-methyl 10 g of active compound/ha; herbicidal effect [%] | Herbicidal effect [%] calculated according to Colby | Herbicidal effect [%] found |
|---|---|---|---|---|
| Chenopodium | 20 | 40 | 52 | 91.3 |
| Festuca ovina | 6.7 | 6.7 | 13 | 68.3 |
| Plantago major | 13.3 | 53.3 | 60 | 86.7 |
| Taraxacum officinale | 20 | 85 | 88 | 98 |
| Poa annua | 0 | 0 | 0 | 28.3 |
| Trifolium repens | 3.3 | 80 | 81 | 94.3 |

Table 7: Herbicide combination according to the invention consisting of pelargonic acid and iodosulfuron-methyl

TABLE 8

| Weed | Pelargonic acid 30000 g of active compound/ha; herbicidal effect [%] | Iodosulfuron-methyl 1 g of active compound/ha; herbicidal effect [%] | Herbicidal effect [%] calculated according to Colby | Herbicidal effect [%] found |
|---|---|---|---|---|
| Chenopodium | 20 | 0 | 20 | 58.3 |
| Festuca ovina | 6.7 | 0 | 7 | 23.3 |
| Plantago major | 13.3 | 0 | 13 | 35 |
| Taraxacum officinale | 20 | 18.3 | 35 | 71.7 |
| Poa annua | 0 | 0 | 0 | 3.3 |
| Trifolium repens | 3.3 | 18.3 | 21 | 36.7 |

Table 8: Herbicide combination according to the invention consisting of pelargonic acid and iodosulfuron-methyl

TABLE 9

| Weed | Pelargonic acid 10000 g of active compound/ha; herbicidal effect [%] | Foramsulfuron 60 g of active compound/ha; herbicidal effect [%] | Iodosulfuron-methyl 10 g of active compound/ha; herbicidal effect [%] | Herbicidal effect [%] calculated according to Colby | Herbicidal effect [%] found |
|---|---|---|---|---|---|
| Chenopodium album | 0 | 13.3 | 40 | 48 | 98.3 |
| Festuca ovina | 0 | 58.3 | 6.7 | 61 | 97 |
| Plantago major | 0 | 33.3 | 53.3 | 69 | 78.3 |
| Taraxacum officinale | 6.7 | 75 | 85 | 97 | 98 |
| Poa annua | 0 | 73.3 | 0 | 73 | 98.3 |
| Trifolium repens | 0 | 60 | 80 | 92 | 95 |

Table 9: Herbicide combination according to the invention consisting of pelargonic acid and also foramsulfuron and iodosulfuron-methyl.

TABLE 10

| Weed | Pelargonic acid 10000 g of active compound/ha; herbicidal effect [%] | Foramsulfuron 15 g of active compound/ha; herbicidal effect [%] | Iodosulfuron-methyl 1 g of active compound/ha; herbicidal effect [%] | Herbicidal effect [%] calculated according to Colby | Herbicidal effect [%] found |
|---|---|---|---|---|---|
| Chenopodium album | 0 | 0 | 0 | 0 | 66.7 |
| Festuca ovina | 0 | 6.7 | 0 | 7 | 68.3 |
| Plantago major | 0 | 0 | 0 | 0 | 41.7 |
| Taraxacum officinale | 6.7 | 45 | 18.3 | 58 | 85 |
| Poa annua | 0 | 18.3 | 0 | 18 | 56.7 |
| Trifolium repens | 0 | 18.3 | 18.3 | 33 | 53.3 |

Table 10: Herbicide combination according to the invention consisting of pelargonic acid and also foramsulfuron and iodosulfuron-methyl.

TABLE 11

| Weed | Pelargonic acid 10000 g of active compound/ha; herbicidal effect [%] | Foramsulfuron 15 g of active compound/ha; herbicidal effect [%] | Iodosulfuron-methyl 10 g of active compound/ha; herbicidal effect [%] | Herbicidal effect [%] calculated according to Colby | Herbicidal effect [%] found |
|---|---|---|---|---|---|
| Chenopodium album | 0 | 0 | 40 | 40 | 95.7 |
| Festuca ovina | 0 | 6.7 | 6.7 | 13 | 85 |
| Plantago major | 0 | 0 | 53.3 | 53 | 81.7 |
| Taraxacum officinale | 6.7 | 45 | 85 | 92 | 98.7 |
| Poa annua | 0 | 18.3 | 0 | 18 | 78.3 |
| Trifolium repens | 0 | 18.3 | 80 | 84 | 95.3 |

Table 11: Herbicide combination according to the invention consisting of pelargonic acid and also foramsulfuron and iodosulfuron-methyl.

TABLE 12

| Weed | Pelargonic acid 10000 g of active compound/ha; herbicidal effect [%] | Foramsulfuron 60 g of active compound/ha; herbicidal effect [%] | Iodosulfuron-methyl 1 g of active compound/ha; herbicidal effect [%] | Herbicidal effect [%] calculated according to Colby | Herbicidal effect [%] found |
|---|---|---|---|---|---|
| Chenopodium album | 0 | 13.3 | 0 | 13 | 78.3 |
| Festuca ovina | 0 | 58.3 | 0 | 58 | 90 |
| Plantago major | 0 | 33.3 | 0 | 33 | 56.7 |
| Taraxacum officinale | 6.7 | 75 | 18.3 | 81 | 95 |
| Poa annua | 0 | 73.3 | 0 | 73 | 92.3 |
| Trifolium repens | 0 | 60 | 18.3 | 67 | 68.3 |

Table 12: Herbicide combination according to the invention consisting of pelargonic acid and also foramsulfuron and iodosulfuron-methyl.

TABLE 13

| Weed | Pelargonic acid 20000 g of active compound/ha; herbicidal effect [%] | Foramsulfuron 45 g of active compound/ha; herbicidal effect [%] | Iodosulfuron-methyl 1.25 g of active compound/ha; herbicidal effect [%] | Herbicidal effect [%] calculated according to Colby | Herbicidal effect [%] found |
|---|---|---|---|---|---|
| Chenopodium album | 10 | 13 | 0 | 22 | 78 |
| Festuca ovina | 0 | 53 | 0 | 53 | 98 |
| Plantago major | 0 | 23 | 3 | 26 | 50 |
| Taraxacum officinale | 7 | 70 | 18 | 77 | 98 |
| Poa annua | 0 | 48 | 0 | 48 | 93 |
| Trifolium repens | 0 | 53 | 32 | 68 | 68 |

Table 13: Herbicide combination according to the invention consisting of pelargonic acid and also foramsulfuron and iodosulfuron-methyl.

TABLE 14

| Weed | Pelargonic acid 20000 g of active compound/ha; herbicidal effect [%] | Foramsulfuron 60 g of active compound/ha; herbicidal effect [%] | Iodosulfuron-methyl 2.5 g of active compound/ha; herbicidal effect [%] | Herbicidal effect [%] calculated according to Colby | Herbicidal effect [%] found |
|---|---|---|---|---|---|
| Chenopodium album | 10 | 13 | 10 | 30 | 89 |
| Festuca ovina | 0 | 58 | 0 | 58 | 98 |
| Plantago major | 0 | 33 | 30 | 53 | 55 |
| Taraxacum officinale | 7 | 75 | 42 | 86 | 97 |
| Poa annua | 0 | 73 | 0 | 73 | 93 |
| Trifolium repens | 0 | 60 | 45 | 78 | 78 |

Table 14: Herbicide combination according to the invention consisting of pelargonic acid and also foramsulfuron and iodosulfuron-methyl.

TABLE 15

| Weed | Pelargonic acid 30000 g of active compound/ha; herbicidal effect [%] | Foramsulfuron 60 g of active compound/ha; herbicidal effect [%] | Iodosulfuron-methyl 10 g of active compound/ha; herbicidal effect [%] | Herbicidal effect [%] calculated according to Colby | Herbicidal effect [%] found |
|---|---|---|---|---|---|
| *Chenopodium album* | 20 | 13.3 | 40 | 58 | 97.7 |
| *Festuca ovina* | 6.7 | 58.3 | 6.7 | 64 | 97.7 |
| *Plantago major* | 13.3 | 33.3 | 53.3 | 73 | 88.3 |
| *Taraxacum officinale* | 20 | 75 | 85 | 97 | 98 |
| *Poa annua* | 0 | 73.3 | 0 | 73 | 85 |
| *Trifolium repens* | 3.3 | 60 | 80 | 92 | 92.3 |

Table 15: Herbicide combination according to the invention consisting of pelargonic acid and also foramsulfuron and iodosulfuron-methyl.

TABLE 16

| Weed | Pelargonic acid 30000 g of active compound/ha; herbicidal effect [%] | Foramsulfuron 15 g of active compound/ha; herbicidal effect [%] | Iodosulfuron-methyl 1 g of active compound/ha; herbicidal effect [%] | Herbicidal effect [%] calculated according to Colby | Herbicidal effect [%] found |
|---|---|---|---|---|---|
| *Chenopodium album* | 20 | 0 | 0 | 20 | 83.3 |
| *Festuca ovina* | 6.7 | 6.7 | 0 | 13 | 78.3 |
| *Plantago major* | 13.3 | 0 | 0 | 13 | 41.7 |
| *Taraxacum officinale* | 20 | 45 | 18.3 | 64 | 96 |
| *Poa annua* | 0 | 18.3 | 0 | 18 | 38.3 |
| *Trifolium repens* | 3.3 | 18.3 | 18.3 | 35 | 53.3 |

Table 16: Herbicide combination according to the invention consisting of pelargonic acid and also foramsulfuron and iodosulfuron-methyl.

TABLE 17

| Weed | Pelargonic acid 30000 g of active compound/ha; herbicidal effect [%] | Foramsulfuron 15 g of active compound/ha; herbicidal effect [%] | Iodosulfuron-methyl 10 g of active compound/ha; herbicidal effect [%] | Herbicidal effect [%] calculated according to Colby | Herbicidal effect [%] found |
|---|---|---|---|---|---|
| *Chenopodium album* | 20 | 0 | 40 | 52 | 93.3 |
| *Festuca ovina* | 6.7 | 6.7 | 6.7 | 19 | 91.7 |
| *Plantago major* | 13.3 | 0 | 53.3 | 60 | 75 |
| *Taraxacum officinale* | 20 | 45 | 85 | 93 | 98.7 |
| *Poa annua* | 0 | 18.3 | 0 | 18 | 73.3 |
| *Trifolium repens* | 3.3 | 18.3 | 80 | 84 | 93.3 |

Table 17: Herbicide combination according to the invention consisting of pelargonic acid and also foramsulfuron and iodosulfuron-methyl.

TABLE 18

| Weed | Pelargonic acid 30000 g of active compound/ha; herbicidal effect [%] | Foramsulfuron 60 g of active compound/ha; herbicidal effect [%] | Iodosulfuron-methyl 1 g of active compound/ha; herbicidal effect [%] | Herbicidal effect [%] calculated according to Colby | Herbicidal effect [%] found |
|---|---|---|---|---|---|
| Chenopodium album | 20 | 13.3 | 0 | 31 | 88.3 |
| Festuca ovina | 6.7 | 58.3 | 0 | 61 | 98.3 |
| Plantago major | 13.3 | 33.3 | 0 | 42 | 63.3 |
| Taraxacum officinale | 20 | 75 | 18.3 | 84 | 98.7 |
| Poa annua | 0 | 73.3 | 0 | 73 | 92.3 |
| Trifolium repens | 3.3 | 60 | 18.3 | 68 | 75 |

Table 18: Herbicide combination according to the invention consisting of pelargonic acid and also foramsulfuron and iodosulfuron-methyl.

The invention claimed is:

1. A herbicide composition comprising
as component (A) an herbicidally active amount of pelargonic acid and
as component (B) at least one ALS inhibitor selected from the group consisting of mesosulfuron-methyl, flazasulfuron, amidosulfuron, ethoxysulfuron and thiencarbazone-methyl, and wherein the composition is synergistically effective, and wherein
when the component (B) used is mesosulfuron-methyl, the weight ratio of components (A) and (B) is in a range of from 4000:1 to 83.3:1, and
when the component (B) used is thiencarbazone-methyl, the weight ratio of components (A) and (B) is in a range of from 3000:1 to 83.3:1, and
when the component (B) used is flazasulfuron, the weight ratio of components (A) and (B) is in a range of from 3000:1 to 50:1, and
when the component (B) used is amidosulfuron, the weight ratio of components (A) and (B) is in a range of from 1000:1 to 41.6:1, and
when the component (B) used is ethoxysulfuron, the weight ratio of components (A) and (B) is in a range of from 500:1 to 12.5:1.

2. The herbicide composition as claimed in claim 1 where, in addition to component (A), at least two different ALS inhibitors are used as component (B).

3. The herbicide composition as claimed in claim 1, comprising an effective amount of components (A) and (B) and additionally one or more further components selected from the group consisting of agrochemically active compounds of a different type, formulation auxiliaries and additives customary in crop protection.

4. The herbicide composition as claimed in claim 1 wherein component (B) used is mesosulfuron-methyl and the weight ratio of components (A) and (B) is in a range of 4000:1 to 333:1.

5. The herbicide composition as claimed in claim 1 wherein component (B) used is thiencarbazone-methyl and the weight ratio of components (A) and (B) is in a range of 3000:1 to 333:1.

6. The herbicide composition as claimed in claim 1 wherein component (B) used is flazasulfuron and the weight ratio of components (A) and (B) is in a range of 3000:1 to 200:1.

7. The herbicide composition as claimed in claim 1 wherein component (B) used is amidosulfuron and the weight ratio of components (A) and (B) is in a range of 1000:1 to 167:1.

8. The herbicide composition as claimed in claim 1 wherein component (B) used is ethoxysulfuron and the weight ratio of components (A) and (B) is in a range of 500:1 to 50:1.

9. A method for controlling weeds, comprising applying a herbicide composition as claimed in claim 1 to the weeds and/or a habitat thereof.

10. The method for controlling weeds as claimed in claim 9 wherein component (A) and component (B) of the herbicide composition are mixed only shortly before application to the weeds and/or a habitat thereof.

11. The method for controlling weeds as claimed in claim 9, wherein component (A) is applied at a rate of at least 2500 g of AS/ha.

* * * * *